(12) United States Patent
Kern (10) Patent No.: US 11,497,863 B2
(45) Date of Patent: Nov. 15, 2022

(54) NEBULIZER UNIT WITH DIRECTLY CONNECTIBLE AMPOULE

(71) Applicant: Stefan Kern, Elsenfeld (DE)

(72) Inventor: Stefan Kern, Elsenfeld (DE)

(*) Notice: Subject to any disclaimer, the term of this patent is extended or adjusted under 35 U.S.C. 154(b) by 432 days.

(21) Appl. No.: 16/475,462

(22) PCT Filed: Dec. 20, 2017

(86) PCT No.: PCT/DE2017/101098
§ 371 (c)(1),
(2) Date: Sep. 10, 2019

(87) PCT Pub. No.: WO2018/121813
PCT Pub. Date: Jul. 5, 2018

(65) Prior Publication Data
US 2019/0388627 A1  Dec. 26, 2019

(30) Foreign Application Priority Data

Jan. 2, 2017 (DE) .................... 10 2017 100 012.7

(51) Int. Cl.
*A61M 11/00* (2006.01)
*A61M 11/04* (2006.01)
*A61M 15/00* (2006.01)

(52) U.S. Cl.
CPC ........... *A61M 11/008* (2014.02); *A61M 11/04* (2013.01); *A61M 15/0028* (2013.01); *A61M 15/0036* (2014.02); *A61M 15/0085* (2013.01); *A61M 2207/00* (2013.01)

(58) Field of Classification Search
CPC ............ A61M 11/005; A61M 15/0028; A61M 15/0031; A61M 15/0036
See application file for complete search history.

(56) References Cited

U.S. PATENT DOCUMENTS 5,682,874 A * 11/1997 Grabenkort ......... A61M 16/183
 128/200.14
5,819,730 A  10/1998 Stone et al.
6,145,703 A  11/2000 Opperman
(Continued)

FOREIGN PATENT DOCUMENTS

CN  101291699 A  10/2008
DE  102005038619 A1  2/2007
(Continued)

OTHER PUBLICATIONS

International Search Report and Written Opinion of PCT/DE2017/101098, dated Apr. 19, 2018.

*Primary Examiner* — Kathryn E Ditmer
(74) *Attorney, Agent, or Firm* — Brian D. Kaul; Westman, Champlin & Koehler, P.A.

(57) ABSTRACT

A nebulizer unit includes a housing, which includes an aerosol generator with a feed chamber disposed at one side, an ampoule receiver, an opening device with at least one opening, which is in communication with the feed chamber, and an ampoule with liquid, which comprises at least one opening, with which it can be inserted or used in the ampoule receiver, wherein the ampoule has a connection region, which interacts with a connector of the ampoule receptacle in order to hold the ampoule firmly in the ampoule receiver and to connect the openings and such that they are leak tight.

16 Claims, 3 Drawing Sheets

(56) References Cited

U.S. PATENT DOCUMENTS

| | | | |
|---|---|---|---|
| 7,029,465 B2* | 4/2006 | Heyes | A61J 1/2089 128/200.14 |
| 7,458,665 B2* | 12/2008 | Batista | B41J 2/17509 222/83 |
| 2003/0140921 A1 | 7/2003 | Smith et al. | |
| 2009/0293868 A1* | 12/2009 | Hetzer | A61M 15/0036 128/200.14 |
| 2011/0146670 A1* | 6/2011 | Gallem | A61M 16/0833 128/200.14 |
| 2012/0037154 A1 | 2/2012 | Gallem et al. | |
| 2014/0166776 A1* | 6/2014 | Fang | A61M 15/0065 239/102.2 |
| 2015/0352297 A1* | 12/2015 | Stedman | A61M 15/0036 128/200.14 |
| 2016/0279351 A1* | 9/2016 | Gallem | A61M 15/0028 |
| 2016/0331913 A1* | 11/2016 | Bourque | A61M 11/042 |
| 2017/0291000 A1* | 10/2017 | Salegui Echeveste | A61M 15/0085 |
| 2019/0143053 A1* | 5/2019 | Chen | A61M 11/005 128/200.14 |

FOREIGN PATENT DOCUMENTS

| | | | | |
|---|---|---|---|---|
| DE | 102008054431 B3 | | 6/2010 | |
| DE | 202010015263 U1 | * | 2/2012 | A61M 15/0065 |
| EP | 287015 A | * | 10/1988 | B05B 9/0838 |
| EP | 2062608 A2 | | 5/2009 | |
| EP | 2987520 A1 | | 2/2016 | |
| WO | 9628205 A1 | | 9/1996 | |
| WO | 02074373 A1 | | 9/2002 | |
| WO | WO-2009111612 A1 | * | 9/2009 | A61M 11/005 |
| WO | WO-2014082818 A1 | * | 6/2014 | A61M 11/005 |
| WO | WO-2014184044 A1 | * | 11/2014 | A61M 11/005 |
| WO | WO-2018040995 A1 | * | 3/2018 | A61M 11/00 |
| WO | 2018121813 A1 | | 7/2018 | |

* cited by examiner

NEBULIZER UNIT WITH DIRECTLY CONNECTIBLE AMPOULE

CROSS-REFERENCE TO RELATED APPLICATIONS

This Application is a Section 371 National Stage Application of International Application No. PCT/DE2017/101098, filed Dec. 20, 2017, the content of which is incorporated herein by reference in its entirety, and published as WO 2018/121813 on Jul. 5, 2018, not in English.

FIELD

Embodiments of the present disclosure relate to a nebulizer unit with ampoule, comprising a housing, which encloses an aerosol generator with feed chamber disposed on one side, an ampoule receiver, an opening device with at least one opening, which is in communication with the feed chamber, and an ampoule with liquid, which has at least one opening, with which it is inserted or can be inserted in the ampoule receiver.

BACKGROUND

In order to treat respiratory tract and lung diseases, an effective medication must be as far a possible completely brought to the place of the disease, that is to say into the bronchial tubes, alveoli or into the air sacs. For this purpose, a medication is usually prepared as a solution and finely atomized by means of a nebulizer before it is inhaled by the patient.

Conventional nebulizers known in the prior art, which are also available as mobile devices, consist of four essential components:

At the heart of the nebulizer is the so-called nebulizer unit, which comprises a microperforated membrane, which by means of a vibration generator, usually a piezo crystal, is set into rapid vibrations, usually in the ultrasonic range, wherein the medication solution bearing directly against the membrane is forced into the micrometer-sized holes of the membrane and is emitted at the output side of the membrane as a mist of fine droplets. Usually, the membrane is mechanically coupled at its circumference to the circular vibration generator directly without or indirectly to a carrier plate, to form a coherent unit, the aerosol generator. Either a tube with mouthpiece or directly a mouthpiece is mounted on the nebulizer unit. Furthermore, a nebulizer comprises a control unit, which generates the signals necessary for actuating the vibration generator. On the feed size of the membrane, integrated into the nebulizer unit, a reservoir for the medication solution is usually located, which provides an adequately dimensioned hollow space, which can usually be firmly closed by means of a cap, so that liquid present in the reservoir is not lost during transport of the nebulizer in the filled condition.

An effective and clearly comprehensible inhalation therapy makes various demands on a nebulizer, in particular as regards hygiene and dosing.

A precise dosage monitoring is important, so that it is ensured that, in the case of the highly effective medication administered by inhalation, the patient also really inhales a dose known to be optimal. The problem here is that, with conventional nebulizers, the user himself must measure out an amount of liquid to be atomized and inhaled from a larger medication container and fill it into the reservoir. Inaccuracies can thereby easily occur. Even if the fluid is already measured out into amounts suitable for inhalation, a part may be lost during refilling from the medication container into the reservoir.

To avoid this, it was proposed to design the medication container as ampoules, which can be inserted directory into an ampoule receiver of the nebulizer unit. For example, the document WO 02/074373 A1 discloses a liquid feed system and a nebulizer equipped therewith, from a housing with an ampoule receiver and a liquid acceptance region. An associated ampoule has, at its upper and lower end, a platelet in each case, which, on removal, leaves behind a well-defined opening in the ampoule. Before insertion, the ampoule is first opened at the lower end by breaking off the platelet there, then inserted and only then is the upper platelet removed to create a ventilation opening.

A disadvantage of this system is that, on improper handling due to opening outside the ampoule receiver, a contamination of the medication liquid with dirt or germs of the user is possible. Furthermore, it is not entirely to be excluded that a portion of the medication liquid is lost before the ampoule can be inserted into the receiver of the feed system that is provided for it.

The invention described in the application document DE 10 2005 038 619 A1 tries to overcome these disadvantages in that it proposes an inhalation therapy device with ampoule, comprising an ampoule receiver, in which the ampoule is inserted while sealed into the receiver and only on insertion is opened by means of an opening device in the form of a pin.

As long as an adequate sealing of the connection of the ampoule and opening device is ensured, losses of medication liquid are thereby minimized and also contamination by germs from the environment are effectively prevented.

Another problem regarding hygiene, however, also remains unsolved with this invention. In order to ensure adequate hygiene, that is to say sterility, the nebulizer should under all circumstances be cleaned and sterilized before each use. With the usually angled construction of conventional nebulizers, however, this is only partially effectively possible, wherein after a certain period of use, or a given number of inhalation sessions, usually some ten times corresponding to approximately two weeks at most, the sterility is no longer adequately ensured.

SUMMARY

One solution would be to replace the nebulizer, or at least the adequately reliably sterilizable parts thereof, in particular the nebulizer unit comprising the aerosol generator, after this maximum reliable duration of use. However, this is problematic since nebulizer units known in the prior art, also and in particular those disclosed in the aforementioned documents, are also very expensive due to their complex construction and a new purchase after the very short use duration of 1-2 weeks would not come into question for the majority of users.

One object of embodiments of the present disclosure is to develop a nebulizer unit, which with at least equal hygiene and dosage accuracy permits user-friendly use and can be simply and inexpensively manufactured.

This object is achieved by means of a nebulizer unit with ampoule according to claim 1, which can be used according to claim 12 and a method for the production thereof according to claim 14.

Embodiments of the present disclosure operate to equip the ampoule with a connection area, by means of which is can be connected directly and indirectly to the nebulizer unit with the aid of the connection means or connector of the ampoule receiver. This does not preclude being able to connect ampoules that comprise a connection region that is not directly compatible with the connection means of the ampoule receiver to the nebulizer unit according to embodiments of the present disclosure via an intermediate-connected adapter.

The connection region of the ampoule can herein be an outer thread, which engages with a correspondingly dimensioned internal thread of the ampoule receiver or it comprises one or more pairs of projecting buttons of a bayonet connector or else an annular bead or groove of a plug connection.

The connection region is herein usually designed in the vicinity of a discharge opening of an inserted ampoule or in the vicinity of a place provided to receive such a discharge opening. For example, the ampoule may have a hollow cylindrical end in which the end face for receiving a discharge opening is provided and on the lateral surface, as a connector or connection means, an outer thread of a screw connection, a pair of buttons of a bayonet connection, an annular bead or an annular groove of a plug connection may be present.

The discharge opening is herein only cut or punched into the material of the ampoule by means of the opening device when the ampoule is connected according to embodiments of the present disclosure. Before insertion and connection, the ampoule is thus completely closed and sealed, thus avoiding contamination or liquid loss.

The form of the ampoule, as well as of the connection region or of the opening are in principle arbitrary. In order to minimize the material consumption for the given liquid volume, however, a rotationally symmetrical ampoule form is ideal, in particular a spherical or at least hollow cylindrical form. To achieve the optimum seal, a circular opening is advisable, since this minimizes the circumference to be sealed for the given opening surface area.

The region coming into contact with the opening device must, for this purpose, consist of adequately soft and cuttable material, for example of plastic or thin metal. The rest of the ampoule, including the connection region, can either be made of the same material, however possibly with different wall thicknesses, the region in which the opening is to be cut being advantageously designed thin-walled in order to facilitate the connection of the ampoule and furthermore to ensure a cleanly defined opening. This is important for the tightness of the connection between the ampoule and nebulizer, in particular if this is only produced by the form-fit between the cut-out opening and the opening device. The rest of the ampoule can be made of one or more other materials. It is herein conceivable to provide a stronger, more rigid material, such as glass or metal. The ampoule can be designed, for example as a glass bottle, which is sealed at its upper end with a seal of metal foil or plastic.

In any case, due to the design, according to embodiments of the present disclosure, of the nebulizer unit and ampoules, additional moving parts and mechanisms that were hitherto required for insertion and connection of ampoules are eliminated. The nebulizer unit according to embodiments of the present disclosure is thereby simpler and considerably more inexpensive to manufacture, which shortens the payback time from the point of view of the user and on the other hand is also considerably less angled, so that the cleaning and sterilization are simplified. It is thus ensured that over a period of use of one to two weeks, one month at most, no or only a very low germ load is present.

After the expiry of this period, the nebulizer unit should be disposed of and replaced with a new one. Because of the more favorable manufacture, this would also be financially acceptable for the majority of users, which significantly increases the chance that this recommendation will also actually be followed.

The use of the nebulizer unit in accordance with embodiments of the present disclosure provides for the insertion of a provided ampoule filled with medication liquid into the ampoule receptacle of the nebulizer as intended and connection to the nebulizer unit by interaction of the connection means of the ampoule receiver with the connection region of the ampoule, so that the discharge opening of the ampoule, which in accordance with embodiment of the present disclosure, was only created on insertion/connection by means of the opening device, is brought into congruence with the inlet opening or openings of the opening device and is connected in a liquid-tight manner.

Depending on the type of connection means and of the connection region, different movement sequences by the user would be necessary. A simple frictional connection between the ampoule and ampoule receiver is the simplest conceivable solution here. Insertion and connection would then be made possible in one operation by means of a straight-line insertion movement. If the ampoule receiver is rotationally symmetrical, an additional rotation during insertion is also made possible, which can be advantageous for example for supporting the opening or cutting action of the opening device.

A screw connection in which an external thread of the ampoule receiver intermeshes with an internal thread of the ampoule receiver requires that the user positions the ampoule in a manner known per se with the end of the thread against the internal thread of the ampoule receiver and, with screwing motions, screws it in, the ampoule being cut open by means of the opening device, at the place provided therefor, for example a region around the rotational axis on a front end face.

In the case of a bayonet connection, a straight-lined insertion followed by a rotational movement would be necessary, the buttons that may be formed on the outer side of the ampoule or on the inner side of the ampoule receiver being first oriented corresponding to the slits. The profile of the slit accordingly has an axially oriented section followed by a principally tangential section, wherein the latter can very well have a non-vanishing angle with the tangential direction in order, for example, to support the cutting operation.

A plug connection with interacting annular bead and annular groove requires a straight-line insertion movement, but with rotationally symmetrical design additionally permits a rotational movement that supports the cutting operation by the opening device. "Annular bead" or "annular groove" in the sense used here is any surrounding elevation or depression, irrespective of whether it has a circular, oval, polygonal or other cross-section.

The production of the nebulizer unit according to embodiments of the present disclosure can be simplified and sped up in that it is composed of two essential components, a front part, which accommodates the aerosol generator and connection means for coupling components such as T pieces or a mouthpiece, as well as a rear part, which comprises an ampoule receiver and an opening device.

For manufacturing a nebulizer unit according to embodiments of the present disclosure, both parts are prepared by forming from corresponding material and possibly installation of the components in a manner known per se. They are then assembled and either detachably or non-detachably connected. The former can be performed by pressing together or plugging together (interlocking or frictional connection), screwing, the latter by adhesive bonding or welding.

Advantageous embodiments of the present invention, which can be realized individually or in combination, in so far as they do not obviously preclude one another are described below.

The connection means of the ampoule receiver and the connection region of the ampoule interacting therewith preferably form a screw connection in which the ampoule receiver comprises an internal and an external region via an external thread intermeshing therewith. Alternatively, the ampoule if fastened by means of a bayonet connection in the ampoule receiver, the pins or buttons, as part of the ampoule receiver, projecting into the inner space thereof or, particularly preferably, being developed as part of the connection region of the ampoule. The slit that interacts with the pins or buttons are correspondingly introduced into the other part in each case, particularly in the ampoule receiver.

The profile of the slit herein comprises known bayonet connections according to at least two regions on a first, essentially axially and a further essentially tangentially oriented region. Further preferred, embodiments of the present disclosure propose, between these two, providing a region with an angle to the tangential direction of 5 to 30 degrees, especially preferably 10 to 20 degrees. By this means, it is achieved that, with insertion and connection of the ampoule in this intermediate region, an axial movement is superimposed on the tangential movement. This may advantageously comprise the squeezing, that is to say the partial compression, of the ampoule by means of a squeezing device, in the simplest case a constriction in the cross-section of the ampoule. Preferably during introduction of the pins in the connection region of the ampoule in the axial portion of the corresponding slit of the ampoule receiver, only slight squeezing, if any, and the essential squeezing takes place in the course of the rotation and the axial displacement of the ampoule takes place during passage through the central, angled slit region.

A further preferred alternative is to make the connection between the ampoule and nebulizer unit by means of a plug connection. This comprises a surrounding annular groove and a corresponding annular bead. The cross-section of the bead is preferably larger than that of the ampoule receiver in the upper region, whereby a squeezing of the ampoule during insertion and connection is ensured.

In some embodiments of the present disclosure, the opening in the opening device, through which the medication liquid flows from the ampoule into the nebulizer unit, communicates, via a feed channel, with the chamber directly upstream of the aerosol generator. This creates more freedom in the constructional design of the nebulizer unit, since the orientation of the ampoule receiver and the opening device that is present therein is independent of the orientation of the aerosol generator. The fluid communication between the two is always ensured by means of the feed channel. It is preferred that the feed opening of the opening unit is in direct communication with the feed chamber, that is to say without interposing a feed channel having a large volume, since this allows the volume to be filled to be minimized and correspondingly a small dimensioned squeezing device or opening device with displacement action is already sufficient.

The opening device of the nebulizer unit according to the unit with ampoule is preferably a pin, which comprises at least one feed opening, which is in fluid communication with the feed chamber disposed upstream of the aerosol generator. Particularly preferably, more than one such feed opening is present. Thereby a given or desired overall opening cross-section, with simultaneously small opening radii, can be realized.

The designation "pin" is intended here to imply that its top side is inclined such that it is longer or higher at one side than on another, for example the opposite, side. The top side may herein be designed to be flat or else, particularly preferred, concavely curved. Thereby, the tip of the pin is more prominent and its cutting action is improved.

Furthermore, the opening device that, by its opening, defines a direction, has a different orientation than the aerosol generator. This direction may thus stand perpendicular to the aerosol generator. Preferably, however, the opening device is oriented at an angle of between 30 and 60 to the aerosol generator. Thus, capillary effects can be minimized and a maximally fast and complete discharge of the medication liquid out of the ampoule is ensured. Here, with the design of the ampoule, care is to be taken that, with a position of the nebulizer that is conventional for inhalation or prescribed, usually such that the nebulizer is essentially horizontal, none of the internal surfaces of the ampoule has a tangential surface that is parallel to the horizontal.

Some embodiments of the present disclosure propose completing a squeezing of the ampoule, or to replace it by an opening device designed as a displacer. Herein, the opening device was designed as an enlarged volume compared to the designs mentioned above. This enters the interior space when the ampoule is closed, where it displaces the medication liquid there out of the ampoule and through the feed opening or openings of the opening device into the feed chamber. Such an embodiment has the further advantage that the possibility also exists of enlarging the contact area between an outside of the opening device and the ampoule inner wall, which is to the advantage of the seal tightness and stability of the connection.

The nebulizer unit further has, on that side of the aerosol generator that faces the feed chamber, an aerosol chamber, which has a discharge opening. To this discharge opening for the aerosol, it is possible to connect various coupling parts, such as, for example, mouthpieces for direct inhalation or else T-pieces of a respiratory system. For example, the housing part forming the aerosol chamber can be embodied as a hollow cylinder in the form of a connection nozzle.

A particularly preferred embodiment of the nebulizer unit provides assembling said nebulizer unit from a front and a rear part. The former herein comprises the aerosol generator as well as the aerosol chamber and connection means for the coupling pieces. The rear part comprises the ampoule receiver with opening device and the feed chamber on the feed side of the aerosol generator or at least the rear part thereof. The two parts are assembled for producing the nebulizer unit according to embodiments of the present disclosure and connected to one another. In the simplest case, the connection is ensured by friction fit. However, a more sophisticated detachable connecting means, such as a plug connection comprising a groove and bead or tongue and groove, a bayonet connection or a screw connection can be provided. However, it is particularly preferred to connect the two parts non-detachably by plugging them together with an adhesively bonded or welded bond. By this means, the best possible tightness is ensure and additional sealing means, such as seal rings on a contact surface between the front and rear parts can be dispensed with. The housing of the nebulizer unit according to embodiments of the present disclosure is preferably made of plastic, in particular a thermoplastic manufactured by injection molding. As welding methods, laser welding or ultrasound welding therefore come into consideration.

In addition to a pure connecting and connection function, the ampoule receiver also has the function of guiding and holding the ampoule. To achieve this more effectively, embodiments of the present disclosure propose equipping it with ampoule guides that have complementary shapes to the ampoule.

Furthermore, in the ampoule receiver, there is preferably present a squeezing device, which is capable of squeezing during introduction and connection, so that, in the interior, a superatmospheric pressure is built up, which is sufficient, after opening, in particular cutting open or punching open, of the ampoule to force an amount of medication liquid out of the ampoule, which corresponds to the volume of the feed chamber and, if appropriate, of the feed channel. The squeezing device may, for example, comprise nubs or a bead projecting out of the ampoule receiver into the interior space, or else in a continually tapering cross-section of the ampoule receiver.

The sealing of the connection between the ampoule and nebulizer unit is preferably ensured by means of a snuggest possible fit of the ampoule, the discharge opening of the ampoule tightly enclosing the opening device. The fact that the region in which the opening device cuts the discharge opening into the wall of the ampoule is made of flexible material contributes to a liquid-tight fit.

The snug fit here could be advantageously supplemented or the requirements thereon reduced if further sealing means, for example a sealing ring, which encloses the feed openings of the opening device and terminates in a planar manner at an end face of the ampoule.

The ampoule of the nebulizer unit according to embodiments of the present disclosure with ampoule is preferably, at least in sections, made of a flexible, easily cuttable but adequately strong and sturdy material, in particular a plastic. This applies in particular to the region in which the discharge opening is to be created. This is preferably generated by the opening device during insertion and connection of the ampoule according to embodiments of the present disclosure. Alternatively the ampoule can also comprise, in the region of the future discharge opening, in particular at its lower end, a break-off tab, which a user breaks off before insertion. Escape of the medication liquid would thereby be ensured by a slight negative pressure in the ampoule.

Furthermore, the ampoule preferably has a circular cross-section, and is particularly preferably rotationally symmetrical in shape, at least in the portion inserted into the ampoule receiver. In particular, the ampoule according to embodiments of the present disclosure is roughly hollow-cylindrical in shape, at least before insertion.

At the upper end, the ampoule is furthermore preferably provided with an ergonomically formed, handle-like thickening for easy grasping and screwing in.

The use according to embodiments of the present disclosure provides that an ampoule filled with medication liquid is provided and, with the connection region first, is inserted into the ampoule receiver of the nebulizer unit according to embodiments of the present disclosure and, according to the particular embodiment of the closure, is connected. During insertion and connection, a discharge opening is simultaneously produced, for example cut out or punched, in the wall of the ampoule, in particular an end face. By the fact that, during cutting or punching, the opening device is pressed in to the opening that is forming, and fills it completely as far as possible, the sealing against the exterior is ensured. The medication liquid can only flow through the feed openings present in the opening device into the feed chamber in front of the aerosol generator.

In some embodiments of the present disclosure, if this discharge is supported by the production of a superatmospheric pressure in the interior of the ampoule, specifically by squeezing an ampoule made of sufficiently flexible material and/or by displacement of the liquid out of the interior of the ampoule by means of an opening device that is designed to be sufficiently voluminous and projects further into the ampoule. The latter offers the advantage, also in the case of ampoules made of stiff material, for example of glass or metal.

The manufacturing method according to embodiments of the present disclosure comprises the provision of a front part, comprising the aerosol generator, and of a rear part comprising the ampoule receiver and opening device. This can be assembled and detachably or non-detachably connected, a non-detachable connection being prepared for reasons of seal-tightness and hygiene. A detachable connection can be achieved by means of a friction fit, bayonet, plug or screw connection. Embodiments of a non-detachable connection include adhesive bonding or, preferably, welding.

Further details and features of embodiments of the present invention are described in greater detail below with reference to the figures of exemplary embodiments. These are only intended to illustrate embodiments of the present disclosure, and in no way to limit its generality,

DETAILED DESCRIPTION OF ILLUSTRATIVE EMBODIMENTS

Figure 1:
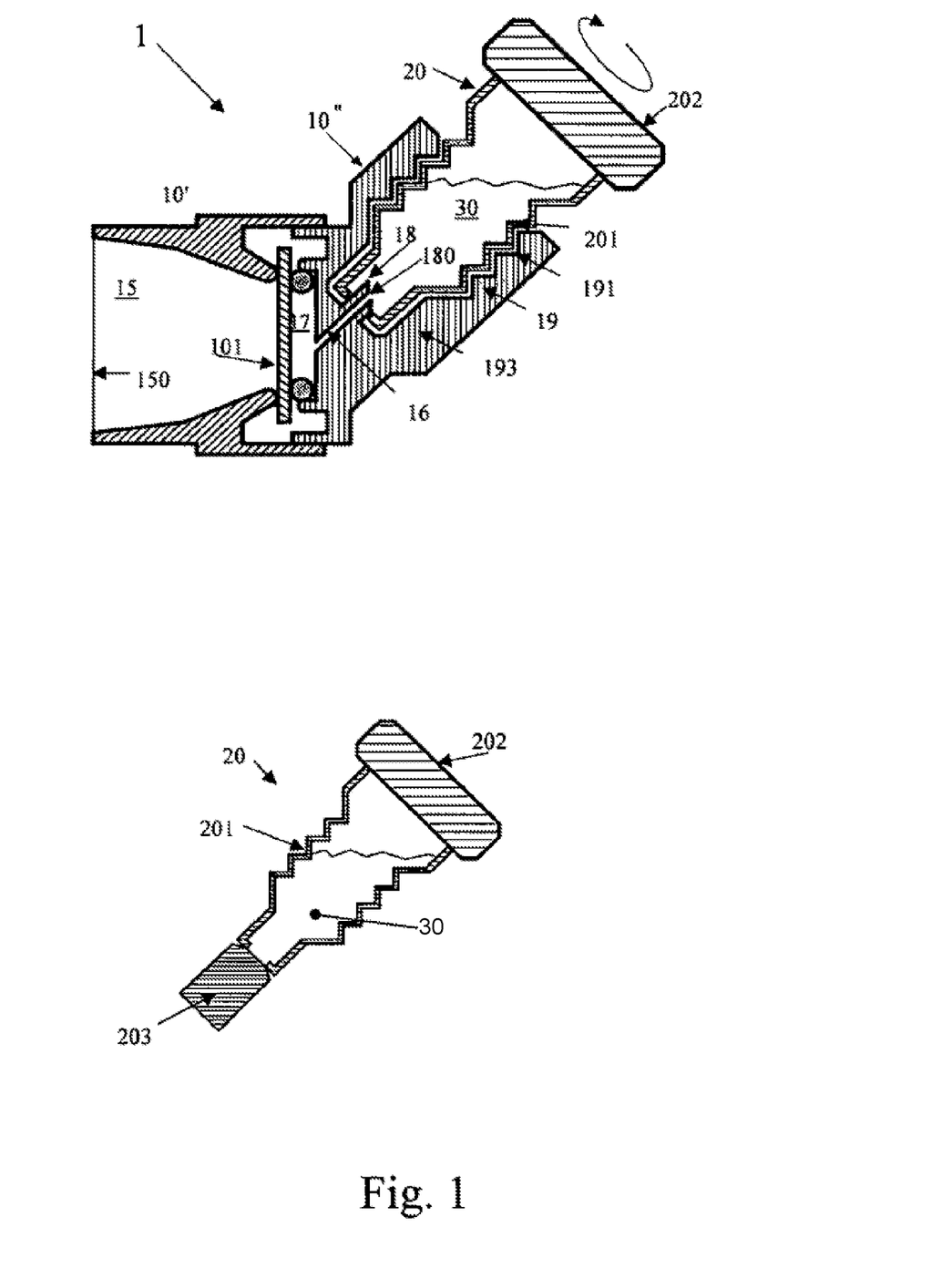
FIG. 1 shows an embodiment of a nebulizer unit according to embodiments of the present disclosure with screw-in ampoule.

FIG. 1 shows a longitudinal section through an embodiment of the nebulizer unit according to embodiments of the present disclosure with ampoule. Housing 10 consisting of front part 10' and rear part 10". The front part 10' accommodates the aerosol generator 101, which is clamped between the front part 10" and the rear part 10". On the feed side of the aerosol generator 101, there is located a feed chamber 17, in which, before atomization, the medication liquid wets the rear side of the aerosol generator. At the discharge side, the aerosol chamber 15 with discharge opening 150 which is enclosed by a region of the housing part 10', which is essentially shaped as a hollow cylinder. By means of this shape, the portion is suitable for coupling to coupling pieces, such as a mouthpiece or else a T-piece of a respiration system. The rearward delimiter of the chamber 17 is formed by an end face of the rear part 10". In this delimiter, there opens the feed opening 180 of the opening device 18, which, like the ampoule receiver 19, is part of the rear part 10". Ampoule receiver 19 comprising, as connection means 19, an internal thread, which intermeshes with an external thread 201 as connection region of an inserted ampoule 20, and thus keeps the ampoule firmly in the ampoule receiver. Opening device 18 a pin with a planar top side and a concentric opening is contacted on its reverse side by the inner rim of the discharge opening 200 of ampoule 20, such that a firm and tight fit is ensured.

The ampoule 20 with medication liquid 30 is essentially rotationally symmetrical and, in this embodiment, comprises a thickening 202 that serves as grip at the top end and a break-off tab 203 at the bottom end. If a user removes the break-off tab 203, a discharge opening 200 is created, which corresponds in its dimensions to the outer dimensions of the opening device 18.

Figure 2:
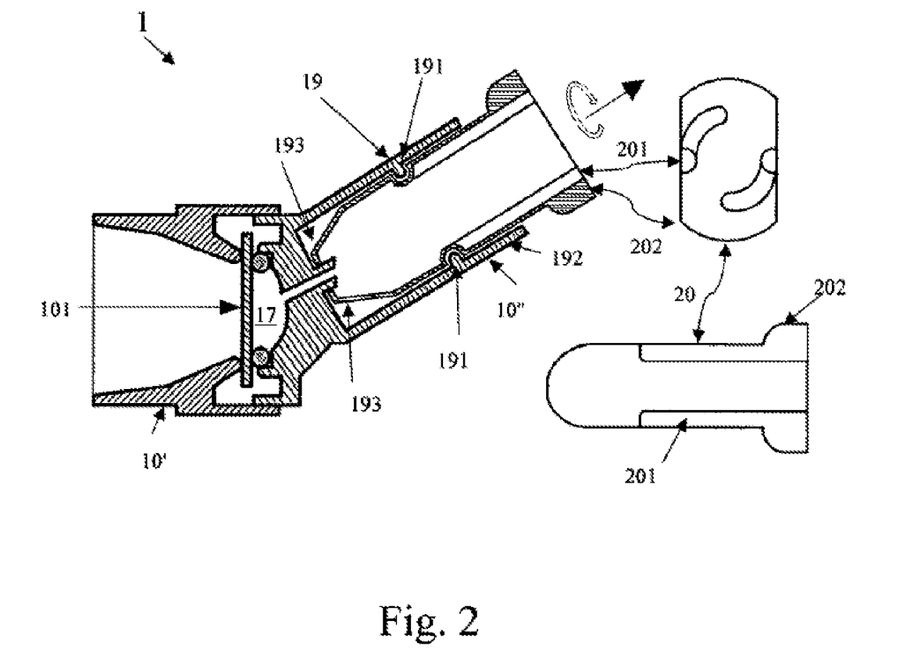
FIG. 2 shows a further embodiment of a nebulizer unit according to embodiments of the present disclosure with ampoule fastened by bayonet closure.

FIG. 2 shows a longitudinal section through an embodiment of the nebulizer unit according to embodiments of the present disclosure with ampoule. Ampoule 20 is fastened by means of a bayonet closure, in which the pins represent the connection means 191 of the ampoule receiver 19. The pins engage in slit 201 in the ampoule 20, which in each case comprise an axial first and a tangential second section, so that the corresponding movement, which is indicated by the double arrow, for insertion and connection of the ampoule 20 is necessary. Ampoule receiver 19 is extended beyond the pins 191. This portion 192 serves for guidance and secure holding of ampoule 20. Here, too, the housing also comprises a front part 10' and a rear part 10".

Opening device 18 is a pin with curved top side, so that the tip projects prominently and can more easily cut the wall of the end face of ampoule 20 in order to create the discharge opening 200. Squeezing device 193 presses or squeezes the front part of the ampoule together, in order to create a superatmospheric pressure in its interior, which forces a portion, corresponding to the volume of the feed chamber, of the liquid 30 outer of the interior of ampoule 20.

Figure 3:
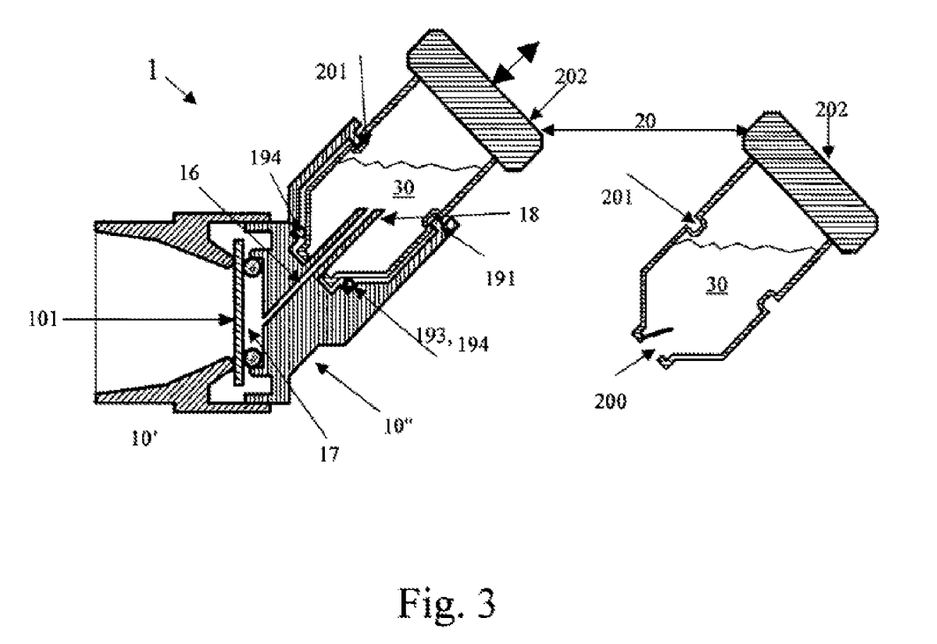
FIG. 3 shows a further embodiment of a nebulizer unit according to embodiments of the present disclosure with ampoule fastened by plug connection.

FIG. 3 shows a further embodiment of the nebulizer unit according to embodiments of the present disclosure with ampoule in the longitudinal section, in which the ampoule is held by means of a plug closure. An annular bead 191 in the ampoule receiver serves as connection means, which interacts with the annual groove 201 in the connection region of the ampoule 20. Ampoule 20 possesses a thickened end in order to avoid an unpleasant point pressure load on the hand of a user during insertion of the ampoule and in addition, on pulling out, to offer a better engagement. Opening device 18 is also designed here as a pin with curved top side, however is considerably more voluminous compared to other designs. By this means it can serve as displacer, which displaces an amount of medication liquid 30 out of the interior of ampoule 20 and, via discharge opening 200, feed opening 180 and feed channel 16, into the feed chamber 17. This permits the use of ampoules made from a few or non-flexible material, such as glass or metal, in which a non-destructive squeezing is not possible. Sealing ring 194 encloses the opening 200 at the lower end of the ampoule 20 and, in addition to the snug fit on the opening device 18, additionally prevents emergence of medication liquid.

Figure 4:
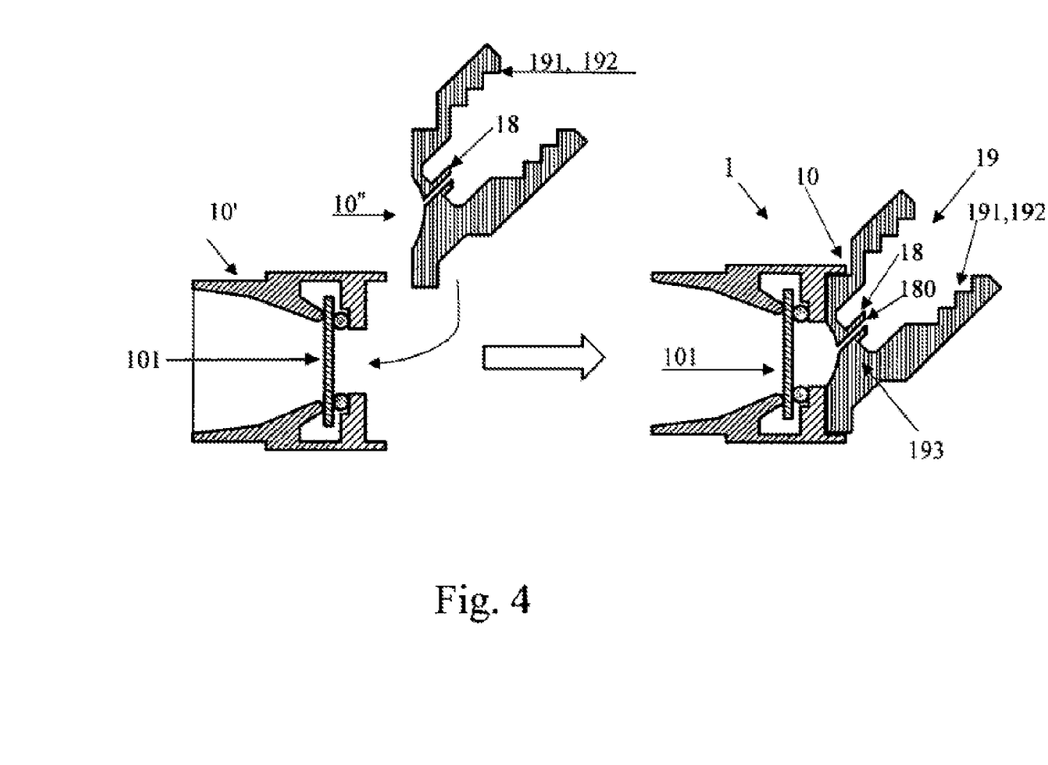
FIG. 4 shows the manufacture of an embodiment of the nebulizer unit according to embodiments of the present disclosure with ampoule consisting of front part and rear part.

FIG. 4 shows in two steps an embodiment of the production of a nebulizer unit comprising a front part and a rear part. The separately manufactured portions 10', 10" are assembled and welded at the contact point in order to form a tight-closing, hygienically enclosing housing 10. The front part 10' holds aerosol generator 101 in its interior. As with all the other illustrated embodiments, the section at the discharge side of the partial housing 10' is manufactured as an approximate hollow cylinder, and permits the connection of coupling parts such as mouthpieces or T-pieces. The rear housing part 10" comprises the ampoule receiver with connection means 191, here in the form of an internal thread of a screw closure, which simultaneously serves as an ampoule guide 192.

LIST OF REFERENCE CHARACTERS

1 Nebulizer unit
10 Housing
10' front part
10" rear part
101 Aerosol generator
15
16 Feed channel
17 Feed chamber
18 Opening device
180 Feed opening
19 Ampoule receiver
191 Connection means
192 Ampoule guide
193 Squeezing device
194 Sealing ring
20 Ampoule
200 Discharge opening
201 Connection region
202 Handle
203 Tab
30 Medication liquid Although the embodiments of the present disclosure have been described with reference to preferred embodiments, workers skilled in the art will recognize that changes may be made in form and detail without departing from the spirit and scope of the present disclosure.

The invention claimed is:

1. A nebulizer unit with ampoule, comprising
a housing, which includes an aerosol generator with a feed chamber disposed at one side,
an ampoule receiver,
an ampoule opening device with at least one opening, which is in communication with the feed chamber, and
an ampoule with liquid, which comprises at least one opening, with which it can be inserted or used in the ampoule receiver,
wherein:
the ampoule has a connection region, which interacts with a connector of the ampoule receiver in order to hold the ampoule firmly in the ampoule receiver and to connect the at least one opening of the ampoule opening device and the at least one opening of the ampoule—in a leak-tight manner;
the housing comprises a front part comprising the aerosol generator and a rear part comprising the ampoule receiver; and
the ampoule receiver comprises a squeezing device, which is suitable for squeezing the ampoule during insertion and keeping it in the squeezed state.

2. The nebulizer unit according to claim 1, wherein the connection region and the connector
are an external thread and an internal thread of a screw connection,
buttons and slits of a bayonet connection, or
an annular bead and annular groove of a plug connection.

3. The nebulizer unit according to claim 1, wherein the at least one opening of the ampoule opening device communicates, in the ampoule opening device, with the feed chamber via the feed channel.

4. The nebulizer unit according to claim 1, wherein the ampoule opening device comprises:
   a pin, and/or
   a pin with a curved top side, and/or
   more than one opening, and/or
   a different orientation than the aerosol generator, and/or
   wherein the ampoule opening device is of such a size that, when the ampoule is completely inserted, a partial volume of the ampoule opening device projecting therein equals the volume of a feed chamber and the volume of the feed channel.

5. The nebulizer unit according to claim 1, wherein on a side of the aerosol generator that is opposite to the feed chamber, there lies an aerosol chamber, which has a discharge opening on one side and, on the other side, is delimited by a portion of the housing.

6. The nebulizer unit according to claim 5, wherein the housing portion that delimits the aerosol chamber
   is essentially a hollow cylinder, and/or
   is prepared for connecting to a mouthpiece or a T-piece.

7. The nebulizer unit according to claim 1, wherein the front part and rear part are
   detachably connected, or
   non-detachably connected.

8. The nebulizer unit according to claim 1, wherein the ampoule receiver comprises ampoule guides, which define an intermediate space within the ampoule receiver that is at least partially complementary in shape and size to the ampoule.

9. The nebulizer unit according to claim 1, wherein a seal between the at least one ampoule opening and ampoule receiver or ampoule opening device is ensured by one or more sealing rings, and/or via a snug fit of the at least one opening of the ampoule on the ampoule opening device.

10. The nebulizer unit according to claim 1, wherein the ampoule:
    when inserted, with a prescribed optimum orientation of the nebulizer unit, only has tangential planes to the surface of the internal volume of the ampoule that form an angle of greater than 0 degrees to the horizontal,
    at an upper end comprises a thickening,
    at a lower end, comprises a table for breaking off,
    is made, at least in sections, of flexible material,
    has a circular cross-section,
    has a rotationally symmetrical shape, and/or
    has a roughly hollow-cylindrical shape when not inserted.

11. The nebulizer unit according to claim 1, wherein the aerosol generator is clamped between the front part and the rear part of the housing.

12. The nebulizer unit according to claim 1, wherein the squeezing device is
    a nub or a bead projecting out of the ampoule receiver into the interior space of the ampoule receiver, or
    a continually tapering cross-section of the ampoule receiver wherein the taper is greater than a taper of the ampoule.

13. A method of using the nebulizer unit according to claim 1, comprising:
    filling the ampoule at least partly with a liquid,
    inserting the ampoule with the connection region into the ampoule receiver of the nebulizer unit, and
    fastening the ampoule using the connector, wherein the at least one ampoule opening and the at least one opening of the ampoule opening device are connected with a tight seal in the ampoule opening device.

14. The method of claim 13, further comprising discharging a portion of the liquid from the ampoule through the at least one opening of the ampoule opening device by squeezing the ampoule using the squeezing device, or by projecting a partial volume of the ampoule opening device into an interior of the ampoule.

15. A method for producing the nebulizer unit according to claim 1, wherein;
    the front part with the aerosol generator, the rear part with the ampoule receiver, and the ampoule opening device are provided,
    assembled, and
    detachably or non-detachably connected to one another.

16. The method according to claim 15, wherein connection of the front part and rear part is produced by means of
    frictional connection, or
    bayonet, plug or screw connection, or
    bonding and/or welding.

* * * * *